US008853162B2

(12) United States Patent
Kurisawa et al.

(10) Patent No.: US 8,853,162 B2
(45) Date of Patent: Oct. 7, 2014

(54) INTERPENETRATING POLYMER NETWORK COMPRISING FIBRIN

(75) Inventors: Motoichi Kurisawa, Singapore (SG); Fan Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 125 days.

(21) Appl. No.: 13/068,481

(22) Filed: May 11, 2011

(65) Prior Publication Data

US 2012/0288564 A1 Nov. 15, 2012

(51) Int. Cl.
| A61K 38/36 | (2006.01) |
| A61P 7/04 | (2006.01) |
| C07K 14/75 | (2006.01) |
| C07K 14/475 | (2006.01) |
| A61L 27/22 | (2006.01) |
| C12P 21/06 | (2006.01) |
| C12N 5/071 | (2010.01) |
| A61L 27/52 | (2006.01) |
| A61K 38/48 | (2006.01) |
| C12N 5/00 | (2006.01) |
| C12P 21/00 | (2006.01) |
| A61K 9/00 | (2006.01) |
| A61L 27/38 | (2006.01) |

(52) U.S. Cl.
CPC .............. A61K 9/00 (2013.01); A61L 27/225 (2013.01); C12P 21/06 (2013.01); C12N 2533/56 (2013.01); C12N 5/069 (2013.01); C12N 2533/80 (2013.01); A61L 27/52 (2013.01); C12N 2537/10 (2013.01); A61K 38/4833 (2013.01); C12N 5/0068 (2013.01); C12P 21/00 (2013.01); A61K 38/363 (2013.01); A61L 27/3808 (2013.01); C12Y 111/01007 (2013.01)
USPC ........................................................ 514/13.6

(58) Field of Classification Search
USPC ........................................................ 514/13.6
See application file for complete search history.

(56) References Cited

PUBLICATIONS

Rowe et al, Interpenetrating Collagen-Fibrin Composite Matrices with Varying Protein Contents and Ratios, 2006, Biomacromolecules, 7(11), 2942-2948, pp. 1-15.*
Lee et al, An injectable hyaluronic acid-tyramine hydrogel system for protein delivery, 2008, Journal of Controlled Release, 134, pp. 186-193.*
Jin, Rong, Injectable Hydrogels for Cartilage Tissue Engineering, 2009, University of Twente, pp. 1-170.*
Ahmed, T.A.E. et al., "Firbin: A Versatile Scaffold for Tissue Engineering Applications", Tissue Engineering Part B: Reviews, Jun. 2008, pp. 199-215, vol. 14, Issue 2.
Aper, T. et al., "Autologous Blood Vessels Engineered from Peripheral Blood Sample", European Journal of Vascular and Endovascular Surgery, Jan. 2007, pp. 33-39, vol. 33, Issue 1.

(Continued)

Primary Examiner — Trevor Love
(74) Attorney, Agent, or Firm — Klarquist Sparkman, LLP

(57) ABSTRACT

There is provided a method of forming a hydrogel, the method comprising: providing a mixture of a polymer comprising a cross-linkable pendant phenolic group, peroxidase, $H_2O_2$, fibrinogen, and thrombin, at concentration sufficient to enzymatically cross-link the polymer and to cleave the fibrinogen to yield fibrin; and allowing the mixture to form a hydrogel. There is also provided a hydrogel comprising a cross-linked network of a polymer interpenetrated by fibrin fibers, the polymer cross-linked by oxidative coupling between phenolic groups pendant on the polymer.

11 Claims, 9 Drawing Sheets

(56) References Cited

PUBLICATIONS

Collen, A. et al., "Influence of fibrin structure on the formatuin and maintenance of capillary-like tubules by human microvascular endothelial cells", Angiogenesis, Jun. 1998, pp. 153-166, vol. 2, No. 2.

Stéphanou, A. et al., "The rigidity in fibrin gels as a contributing factor to the dynamics of in vitro vascular cord formation", Microvascular Research, May 2007, pp. 182-190, vol. 73, Issue 3.

Bauters, C. et al., "Site-specific therapeutic angiogenesis after systemic administration of vascular endothelial growth factor", Journal of Vascular Surgery, Feb. 1995, pp. 314-325, vol. 21, No. 2.

Baffour, R. et al., "Enhanced angiogenesis and growth of collaterals by in vivo administration of recombinant basic fibroblast growth factor in a rabbit model of acute lower limb ischemia: Dose-response effect of basic fibroblast growth factor", Journal of Vascular Surgery, Aug. 1992, pp. 181-191, vol. 16, No. 2.

Bensaïd, W. et al., "A biodegradable fibrin scaffold for mesenchymal stem cell transplantation", Biomaterials, Jun. 2003, pp. 2497-2502, vol. 24, Issue 14.

Vailhé, B. et al., "The formation of tubular structures by endothelial cells is under the control of fibrinolysis and mechanical factors", Angiogenesis, Dec. 1998, pp. 331-344, vol. 2, No. 4.

Cholewinski, E. et al., "Tranexamic Acid An Alternative to Aprotinin in Fibrin-Based Cardiovascular Tissue Engineering", Tissue Engineering Part A, Nov. 2009, pp. 3645-3653, vol. 15, Issue 11.

Chen, W.Y.J.J. and Abatangelo, G., "Functions of hyaluronan in wound repair", Wound Repair and Regeneration, Mar. 1999, pp. 79-89, vol. 7, Issue 2.

Deed, R. et al., "Early respinse gene signaling is induced by angiogenic oligosaccharides of hyaluronan in endothelial cells. Inhibition by non-angiogenic, high molecular weight hyaluronan", International Journal of Cancer, Apr. 10, 1997, pp. 251-256, vol. 71, Issue 2.

Phelps, E.A. et al., "Bioartificial matrices for therapeutic vascularization", Proceedings of the National Academy of Sciences, Feb. 23, 2010, pp. 3323-3328, vol. 107, No. 8.

Pardue, E.L. et al., "Role of hyaluronan in angiogenesis and its utility to angiogenic tissue engineering", Organogenesis, Oct.-Dec. 2008, pp. 203-214, vol. 4, Issue 4.

Lee, F. et al., "An injectable enzymatically cross-linked hyaluronic-acid-tyramine hydrogel system with independent tuning of mechanical strength and gelation rate", Soft Matter, 2008, pp. 880-887, vol. 4, Issue 4.

Fournier, N. and Doillon, C.J., "In vitro angiogenesis in fibrin matrices containing fibronectin or hyaluronic acid", Cell Biology International Reports, 1992, pp. 1251-1263, vol. 16, Issue 12.

Fraser, J.R.E. et al., "Hyaluronan: its nature, distribution, functions and turnover", Journal of Internal Medicine, Jun. 1997, pp. 27-33, vol. 242, Issue 1.

Furst, W. et al., "Comparison of structure, strength and cytocompatibility of a fibrin matrix supplemented either with tranexamic acid or aprotinin", Journal of Biomedical Materials Research, Part B: Applied Biomaterials, Jul. 2007, pp. 109-114, vol. 82, Issue 1.

Jockenhoevel, S. et al., "Tissue engineering: complete autologous valve conduit—a new moulding technique", Thorac Cardiovasc Surg, Mar. 2001, pp. 287-290, vol. 49, Issue 5.

Urech, L. et al., "Mechanical properties, proteolytic degradability and biological modifications affect angiogenic process extension into native and modified fibrin matrices in vitro", Biomaterials, Apr. 2005, pp. 1369-1379, vol. 26, Issue 12.

Nakatsu, M.N. et al., "Angiogenic sprouting and capillary lumen formation modeled by human umbilical vein endothelial cells (HUVEC) in fibrin gels: the role of fibroblasts and angiopoietin-1", Microvascular Research, Sep. 2003, pp. 102-112, vol. 66, Issue 2.

Montesano, R., et al., "Synergistic effect of hyaluronan oligosaccharides and vascular endothelial growth factor on angiogenesis in vitro", Laboratory Investigation, 1996, pp. 249-262, vol. 75.

Nakatsu, M.N. et al., "Optimized fibrin gel bead assay for the study of angiogenesis", Journal of Visualized Experiments, 2007, p. 186 (2 pages), vol. 3.

Nehls, V. and Drenckhahn, D., "A microcarrier-based cocultivation system for the investigation of factors and cells involved in angiogenesis in three-dimensional fibrin matrices in vitro", Histochemistry and Cell Biology, Dec. 1995, pp. 459-466, vol. 104, No. 6.

Pankajakshan, D. et al., Vascular tissue generation in response to signaling molecules integrated with a novel poly(epsilon caprolactone)-fibrin hybrid scaffold:, Journal of Tissue Engineering and Regenerative Medicine, Sep.-Oct. 2007, pp. 389-397, vol. 1, Issue 5.

Thiagarajan, P. et al., "Alternative Adhesion Sites in Human Fibrinogen for Vascular Endothelial Cells", Biochemistry, Apr. 2, 1996, pp. 4169-4175, vol. 35, Issue 13.

Rooney, P. et al., "The role of hyaluronan in tumour neovascularization", International Journal of Cancer, Mar. 3, 1995, pp. 632-636, vol. 60, Issue 5.

Sattar, A. et al., "Application of angiogenic oligosaccharides of hyaluronan increase blood vessel numbers in rat skin", Journal of Investigative Dermatology, Oct. 1994, pp. 576-579, vol. 103, No. 4.

Soker, S. et al., "Systems for therapeutic angiogenesis in tissue engineering", World Journal of Urology, Feb. 2000, pp. 10-18. vol. 18, No. 1.

Sieminski, A.L. et al., "The relative magnitudes of endothelial force generation and matrix stiffness modulate capillary morphogenesis in vitro", Experimental Cell Research, Jul. 15, 2004, pp. 574-584, vol. 297, Issue 2.

Tammi, M.I. et al., "Hyaluronan and Homeostasis: A Balancing Act", The Journal of Biological Chemistry, Feb. 15, 2002, pp. 4581-4584, vol. 277, Issue 7.

Ahmed, T.A.E. et al., "Characterization and Inhibition of Fibrin Hydrogel-Degrading Enzymes During Development of Tissue Engineering Scaffolds", Tissue Engineering, Jul. 2007, pp. 1469-1477, vol. 13, No. 7.

Lokeshwar, V.B. and Selzer, M.G., "Differences in Hyaluronic Acid-mediated Functions and Signaling in Arterial, Microvessel, and Vein-derived Human Endothelial Cells", The Journal of Biological Chemistry, Sep. 8, 2000, pp. 27641-27649, vol. 275, Issue 36.

Nehls, V. and Drenckhahn, D., "A Novel, Microcarrier-based in Vitro Assay for Rapid and Reliable Quantification of Three-dimensional Cell Migration and Angiogenesis", Microvascular Research, Nov. 1995, pp. 311-322, vol. 50, Issue 3.

Nehls, V. and Herrmann, R., "The Configuration of Fibrin Clots Determines Capillary Morphogenesis and Endothelial Cell Migration", Microvascular Research, May 1995, pp. 347-364. vol. 51, Issue 3.

Hayen, W. et al., "Hyaluronan stimulates tumor cell migration by modulating the fibrin fiber architecture", Journal of Cell Science, Jul. 1, 1999, pp. 2241-2251, vol. 112, Issue 13.

Ye, Q. et al., "Fibrin gel as a three dimensional matrix in cardiovascular tissue engineering", European Journal of Cardio-Thoracic Surgery, May 2000, pp. 587-591, vol. 17, Issue 5.

Zhao, H. et al., "A polylactide/fibrin gel composite scaffold for cartilage tissue engineering: fabrication and an in vitro evaluation", Journal of Materials Science: Materials in Medicine, Jan. 2009, pp. 135-143, vol. 20, No. 1.

Wang, L.S. et al., "Injectable biodegradable hydrogels with tunable mechanical properties for the stimulation of neurogenesic differentiation of human mesenchymal stem cells in 3D culture", Biomaterials, Feb. 2010, pp. 1148-1157, vol. 31, Issue 6.

Shikanov, A. et al., "Interpenetrating fibrin-alginate matrices for in vitro ovarian follicle development", Biomaterials, Oct. 2009, pp. 5476-5485, vol. 30, Issue 29.

Lee and Kurisawa, 2013, "Formation and stability of interpenetrating polymer network hydrogels consisting of fibrin and hyaluronic acid for tissue engineering", Acta Biomaterialia, 9: 5143-5152.

Iruela-Arispe, 2005, "The Cell Biology of Angiogenesis," Angiogenesis, pp. 1-30.

\* cited by examiner

Table 1. Gel compositions and concentrations of materials used

| Gel Type | Gel Composition | Schematic of Gel Structure |
|---|---|---|
| Fibrin Gel | 2.5 mg/ml of fibrinogen treated with 0.24 unit/ml of thrombin |  |
| Fibrin Gel + HAT conjugates | 2.5 mg/ml of fibrinogen treated with 0.24 unit/ml of thrombin, containing 2.5 mg/ml of uncross-linked HAT polymer | 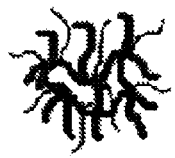 |
| HAT Gel | 2.5 mg/ml of HAT was cross-linked with $H_2O_2$ and 0.062 unit/ml of HRP | 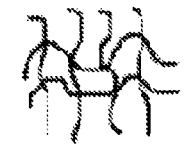 |
| HAT-Fibrin Gel | Both HAT and fibrin are cross-linked; HAT was cross-linked with $H_2O_2$ and 0.062 unit/ml of HRP and fibrinogen was treated with 0.24 unit/ml of thrombin |  |

FIGURE 9

INTERPENETRATING POLYMER NETWORK COMPRISING FIBRIN

FIELD OF THE INVENTION

The present invention relates to hydrogel materials that may be useful as scaffold material for angiogenesis, including hydrogels that comprise fibrin.

BACKGROUND OF THE INVENTION

Vascular tissue engineering is becoming an important area of research in recent years due to pathological diseases (e.g. diabetic blindness, gangrene) resulting from deficient angiogenesis. Angiogenesis is a natural biological process that involves the formation of new blood capillaries from pre-existing ones (Nakatsu et al., 2003), providing adequate blood supply for tissues to obtain nutrients and oxygen for survival. In healthy individuals, angiogenesis is regulated through the production of a balanced amount of growth and inhibitory factors. The loss of this balance results in formation of excessive or insufficient blood capillaries, both of which are directly related to pathological diseases. Excessive formation of blood capillaries support tumor metastasis to other regions of the body (Stephanou et al., 2006), whereas a lack of new blood capillary formation hinders the growth and development of tissues, eventually leading to pathology (e.g. in cases of heart failure, diabetic blindness, and gangrene).

Organ transplants and blood vessel prosthesis are ways in which such clinical conditions caused by a lack of angiogenesis can be treated. However, these may not be ideal treatment options due to the diminishing availability of organs and the high risk of infection that prosthetic blood vessels may bring. Autografts have also been clinically used for the replacement of damaged blood vessels. However, such a procedure is not popular because it requires multiple operations.

Therefore, the current approach to treating such diseases involves inducing the formation of blood vessels by re-initiating the angiogenic process. Current methods used include in vivo gene therapy via the injection of plasmids containing VEGF and bFGF cDNA into ischemic tissues (Bauters et al., 1994), and targeted in vivo injection of growth factor proteins in its soluble form (Baffour et al., 1992). These approaches may be less effective than desired due to diffusion of growth factors away from the ischemic site following injection (Phelps et al., 2009).

Current efforts in tissue engineering focus on development of hydrogels to support the formation of neo-vessels. Hydrogels are synthetic three-dimensional, biodegradable scaffolds that may be used to encapsulate growth factors to induce proliferation and migration of endothelial cells from quiescent vessels into the matrix. Alternatively, cells can be encapsulated within a hydrogel and prevascularization is stimulated before implantation of hydrogel into the host.

A variety of hydrogels have been proposed for vascular tissue engineering, some of which include fibrin gel, collagen gels, and gels formed using synthetic polymers (e.g. polyethylene glycol, dextran) (Sieminski et al, 2004; Moon et al., 2009; Phelps et al., 2009).

Most research focuses on the use of fibrin gel as a matrix for stimulating blood vessel formation (Collen et al., 1998; Nakatsu et al., 2003; Urech et al, 2004). Fibrin, a naturally occurring clotting material involved in the process of blood coagulation is a popular biodegradable scaffold used in vascular tissue engineering due to its ability to support cell adhesion and proliferation, and most importantly, angiogenesis.

Furthermore, autologous fibrinogen, the precursor of fibrin, can be isolated from the patient's own blood, thus avoiding the risks of immune rejections (Aper et al., 2006; Jockenhoevel et al., 2001). In addition, fibrinogen contains integrin $\alpha_v\beta_3$ (Perumal et al., 1996) and cell adhesion molecules like L1 and ephrin B2 that allow the adhesion of endothelial cells, thereby, facilitating their spreading, traction, and proliferation on the fibrin fibers.

However, fibrin is degraded rapidly by proteases such as plasmin and matrix metalloproteinases (MMPs), undermining its potential as a tissue engineering scaffold, as it is desirable for the fibrin gel shape to remain intact until mature vessels can be formed. Previously, protease inhibitors have been used to overcome the rapid rate of degradation. The use of aprotinin, a protease inhibitor derived from bovine, however, has been suspended recently due to associations with serious adverse effects. Tranexamic acid, an alternative fibrinolysis inhibitor, is also associated with side effects (Furst et al., 2006). Increasing the concentration of fibrinogen in order to improve degradation resistance leads to an increased mechanical strength, and may result in a gel with too great a stiffness that is not suitable for supporting capillary formation.

Several studies have also reported the successful formation of angiogenic sprouts observed in fibrin gels (Collen et al., 1998; Urech et al., 2004). In contrast, in vitro angiogenesis models using collagen gels or matrigel failed to model the formation of sprouts. Any lumens that were observed were thin and slit-like in appearance (Nakatsu et al., 2003). Furthermore, human umbilical vein endothelial cell (HUVEC), widely known as the canonical cell line for in vitro angiogenesis assays, responded most efficiently to interactions with fibrin (Ingber and Folkman, 1989).

Thus, there exists a need for an alternative tissue scaffold that can be used to support angiogenesis.

SUMMARY OF THE INVENTION

Hydrogels containing different biomaterials and compositions that support vessel formation for therapeutic angiogenesis have been a focus of research in the recent years. The properties of the hydrogel, such as stiffness, porosity, and fibrin fiber network, influence how cells respond to and manipulate the matrix in which the cells are embedded, enabling the cells to migrate, proliferate, and self arrange into the proper structures to form blood vessels. On the one hand, stiffness allows the gel to resist the forces exerted by migrating cells, while on the other hand, softness provides a gel in which the cells can proliferate and reorganise into vessels.

The present invention relates to a composite hydrogel composed of interpenetrating networks of fibrin and cross-linked polymer. The polymer is cross-linked around fibrin fibers, thus limiting the size of the fibers and providing a structural support for the easily degraded fibrin. The addition of a cross-linked polymer that interpenetrates the fibrin as it is formed thus modifies the fibrin network structure. This combination of cross-linked polymer surrounding fibrin fibers allows for cell migration within the scaffold but also provides a support within the hydrogel that exhibits greater resistant to proteolytic degradation and lends stiffness to the hydrogel.

The hydrogels are formed by treating fibrinogen with thrombin to yield fibrin while at the same time cross-linking a polymer that contains pendant, cross-linkable phenolic groups using enzymatic oxidative cross-linking.

The hydrogels of the invention may be injectable, biocompatible and biodegradable. The hydrogels may demonstrate improved resistance to fibrinolytic degradation as compared to fibrin hydrogels. Thus the hydrogels may be useful as biomaterial for vascular tissue engineering and may be used to support angiogenesis in vivo.

In one aspect, there is provided a method of forming a hydrogel, the method comprising: providing a mixture of a polymer comprising a cross-linkable pendant phenolic group, peroxidase, $H_2O_2$, fibrinogen, and thrombin, at concentration sufficient to enzymatically cross-link the polymer and to cleave the fibrinogen to yield fibrin; and allowing the mixture to form a hydrogel.

The polymer may comprise hyaluronic acid or dextran comprising a cross-linkable pendant phenolic group. The hyaluronic acid may be, for example, a hyaluronic-tyramine conjugate.

The pendant phenolic group may be a flavonoid, a tyramine group or a hydroxyphenylpropionic acid.

In some embodiments, the mixture comprises the hyaluronic acid at a concentration of about 1 mg/ml to about 20 mg/ml, a peroxidase at a concentration of about 0.01 unit/ml to about 0.5 unit/ml, hydrogen peroxide at a concentration of about 20 µM to about 1000 µM, the fibrinogen at a concentration of about 1 mg/ml to about 10 mg/ml, and the thrombin at a concentration of about 0.1 unit/ml to about 2.0 unit/ml.

Cells, an angiogenic protein or a therapeutic agent may be included in the mixture prior to allowing the mixture to form a hydrogel. The cells may be any cells capable of undergoing angiogenesis.

In some embodiments, the method comprises first providing a mixture of a polymer comprising the cross-linkable pendant phenolic group and the fibrinogen, and then subsequently adding the peroxidase, $H_2O_2$ and thrombin prior to allowing the mixture to form a hydrogel.

In another aspect of the present invention, there is provided a hydrogel comprising a cross-linked network of a polymer interpenetrated by fibrin fibers, the polymer cross-linked by oxidative coupling between phenolic groups pendant on the polymer.

The hydrogel may be formed according to the methods as described herein.

In a further aspect, the present invention provides a method of promoting angiogenesis, the method comprising: contacting a population of cells capable of undergoing angiogenesis with the hydrogel of the invention under conditions sufficient for the population of cells to undergo angiogenesis.

The population of cells may be encapsulated in the hydrogel, and may be in vitro or in vivo. If the population of cells in a subject, the contacting may comprise administering the hydrogel to the subject.

The method may further comprise administering the hydrogel to a subject.

In yet another aspect, there is provided a method of culturing a cell, the method comprising contacting a cell with the hydrogel of the invention under conditions sufficient for the population of cells to grow.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The figures, which illustrate, by way of example only, embodiments of the present invention, are as follows.

FIG. 9. Table 1 is shown, which contains information relating to gel compositions and concentrations of materials used.

DETAILED DESCRIPTION

Figure 1:
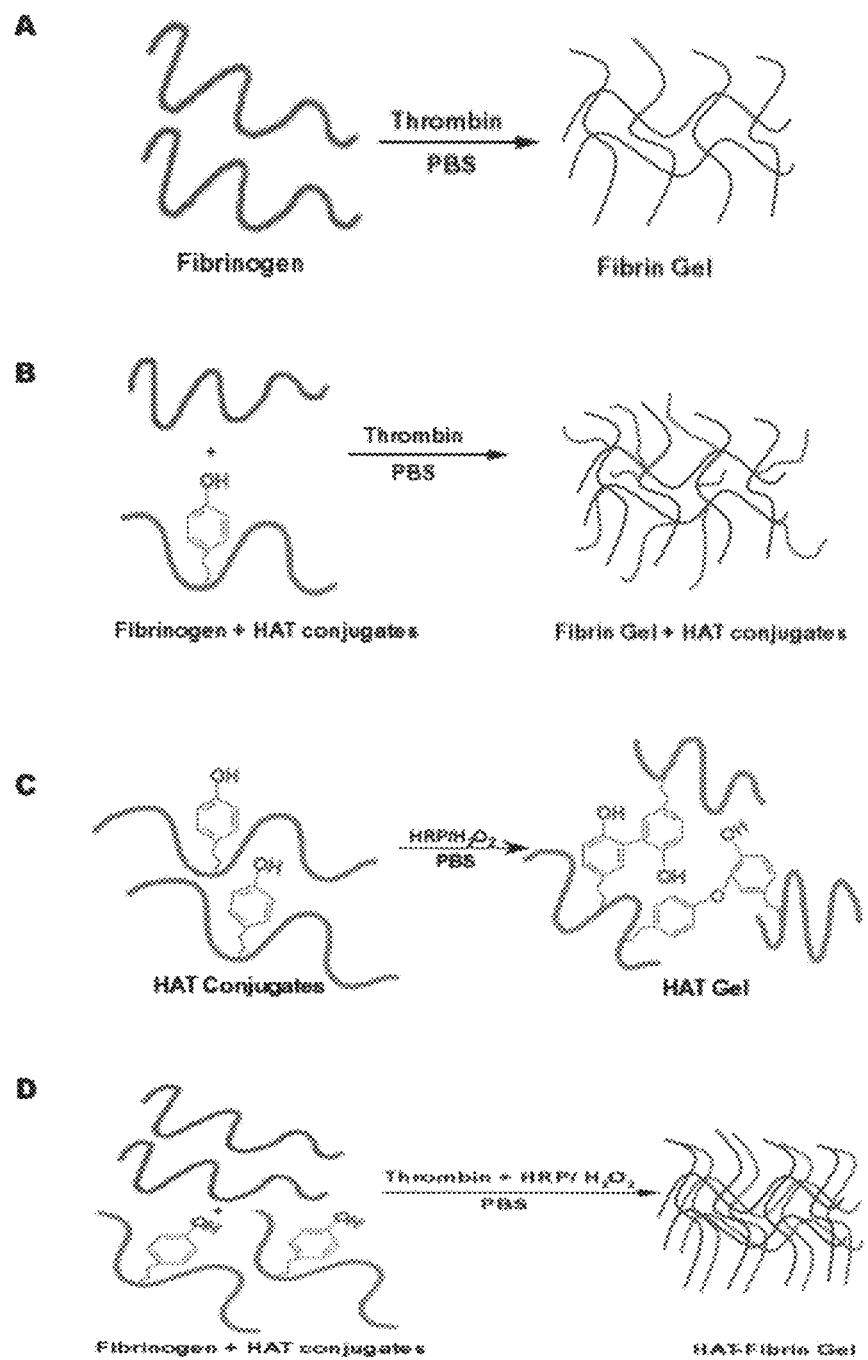
FIG. 1. A schematic depiction of formation of the various types of gel tested. A: fibrin gel; B: fibrin gel+hyaluronic acid-tyramine (HAT) conjugates; C: cross-linked HAT gel; D: interpenetrating cross-linked HAT and fibrin gel.

There is provided a method of forming a hydrogel. A hydrogel with interpenetrating polymer networks composed of a polymer comprising a pendant phenolic group and fibrin is formed using the oxidative coupling of phenol moieties enzymatically catalyzed by oxidative coupling.

The method comprises combining a polymer having a pendant phenolic group with fibrinogen, and using peroxidase and thrombin to form a cross-linked polymer and fibrin, respectively. By forming the polymer and fibrin together, the polymer is cross-linked around the newly forming fibrin fibers, creating an interpenetrating network of the two. This network is then subsequently allowed to gel, thus providing the resultant hydrogel.

As will be appreciated, a hydrogel refers to a polymeric matrix that is or that can become highly hydrated, thus absorbing a liquid such as water. Hydrogels for example, include highly hydrated suspensions comprised of a cross-linked network of hydrophilic polymeric molecules dispersed within water or an aqueous solution; the structural arrangement of such a hydrogel derives from cross-links formed between the molecules by various chemical and physical bonds. As used herein, a hydrogel may refer to either the polymeric matrix with any absorbed liquid, or the polymeric matrix in its dry state (i.e. without absorbed liquid), which may be subsequently hydrated.

Thus, in the method, a reaction mixture is mixed, comprising the polymer comprising a pendant phenolic group, peroxidase to cross-link the polymer, $H_2O_2$, fibrinogen and thrombin to cleave the fibrinogen to fibrin, and any cofactors or reactants required by the enzymes to catalyse the respective reactions.

The polymer is chosen as a biocompatible polymer that may be biodegradable and which may have low immunogenicity. The polymer may be a biological polymer, for example a substance naturally found in a cell or in a body of an organism. The polymer may be a biological polymer naturally found in a subject to whom the hydrogel is to be administered for inducing angiogenesis within the subject. In particular embodiments, the polymer is hyaluronic acid comprising a pendant phenolic group or is dextran comprising a pendant phenolic group. For example, the hyaluronic acid having a pendant phenolic group may be a hyaluronic acid-tyramine conjugate (HA-Tyr). In other embodiments, the polymer may be chitin, chitosan, heparin, gelatin, collagen or PEG, having a pendant phenolic group available for cross-linking.

Where the polymer does not normally include a pendant phenolic group, the polymer is modified to have one or more types of pendant phenolic groups. Such modifications to append phenolic groups are known and are within the capabilities of a person of ordinary skill. Thus, hyaluronic acid may be conjugated with tyramine to yield hyaluronic acid-tyramine.

The pendant phenolic group is any pendant group that contains a cross-linkable phenol group, meaning that the phenol group on the pendant group is available for cross-linking with an adjacent phenol group on the same or different polymer molecule. For example, the pendant phenolic group may be a tyramine group, a flavonoid such as catechin or epigallocatechin gallate, or hydroxyphenylpropionic acid (HPA), such as 3,4-hydroxyphenylpropionic acid. Any combination of cross-linkable pendant phenolic groups may be included in the polymer.

Peroxidase is included in the reaction to cross-link the polymer; peroxidase catalyses an oxidative reaction that results in coupling of phenol groups within the polymer, either phenol groups on the same polymer molecule or phenol groups on different polymer molecules. The peroxidase may be any peroxidase, for example, in one embodiment the peroxidase is horse-radish peroxidase (HRP).

It will be appreciated that any cofactors or substrates required by peroxidase will be included in the reaction mixture. For example peroxidase uses peroxide such as $H_2O_2$ to catalyse an oxidative reaction, and thus $H_2O_2$ is included in the reaction mixture.

Fibrinogen is also included in the reaction mixture, and may be fibrinogen obtained from a subject to whom the hydrogel (or reaction mixture prior to gelling) is to be administered in order to promote angiogenesis within the subject.

Thrombin is included in the reaction mixture in order to proteolytically process the fibrinogen to yield fibrin. Upon thrombin cleavage, fibrinogen forms fibrin which aggregates to form fibers. If desired, the fibrin may also be cross-linked, for example, by inclusion of a protein factor that catalyses cross-linking of fibrin, such as factor XIII.

Enzymes used to cross-link the polymer, thrombin, fibrinogen and any other factors or cofactors for catalysing the cross-linking and the formation of fibrin are readily commercially available. The polymer having a pendant phenolic group may be prepared using known methods, including using a commercially available polymer which may be modified to incorporate pendant phenolic groups that are available for cross-linking. See for example, Fan Lee et al., 2008; WO 2009148405; and WO 2010138082.

The reaction mixture is prepared in a suitable buffer in which the cross-linking and fibrinogen cleavage reactions may occur, and including cofactors required by the enzymes included in the reaction mixture. The pH of the reaction mixture is chosen to be a pH that is conducive to both the cross-linking of the polymer and the cleavage of fibrinogen. A suitable pH can readily be determined using minimal routine laboratory work, for example as set out in Example 1 below. In some embodiments, the pH of the reaction mixture is from about 6.0 to about 8.0, or is from about 7 to about 7.9. Thus, the buffer chosen will be suitable to maintain the desired pH to promote enzymatic activity and to allow formation of the hydrogel. In one embodiment, the buffer may be PBS, and the reaction mixture may be buffered to between pH 7.4 to 7.8.

The components are mixed together in the reaction mixture at a concentration sufficient to cross-link the polymer and to form the fibrin fibers. The concentrations of the various components within the reaction mixture will affect the final properties of the resulting hydrogel. A person of ordinary skill will be able to adjust the concentrations of the various components in order to provide a hydrogel with desired properties such as stiffness, porosity, resistance to degradation, using routine laboratory techniques, for example techniques as described in Example 1 below. The particular concentrations of the various components may depend on the application or context in which the resulting hydrogel is to be used. As well, the characteristics and concentrations of one component may influence the concentration of another component included in the reaction mixture. For example, having a greater concentration of $H_2O_2$ may allow for a lower concentration of peroxidase or a lower degree of substitution of phenolic groups pendant on the polymer.

When the hydrogel is to be used as a scaffold for angiogenesis, it may be desirable to strike a balance between a hydrogel that is sufficiently stiff to withstand the forces exerted by migrating cells and a hydrogel having sufficient porosity to allow for formation of vessel-like structures. It has been found that when seeded on fibrin gels, endothelial cells were reported to exert cell traction forces and secrete proteases like plasmin and matrix metalloproteinases (MMPs) to degrade the fibrin (Tamer et al., 2007), thus assisting the cells to migrate and providing space for the cells to orient into pre-angiogenic-like structures. Although softer fibrin gels are better at supporting the formation of capillary like structures, a higher mechanical strength of fibrin fibers allows the fibrin matrix to withstand the cell traction forces and proteolytic effect of the secreted enzymes (Shay et al., 2000). Cell migration is important and is part of the angiogenic process that eventually leads to vessel formation. Thus, gel porosity, fibrin fiber structure, and gel stiffness can affect the ability of cells to transit from one phase to another in the angiogenic process (i.e., from cell migration to proliferation, alignment, tube formation, anastomosis).

Thus, the degree of cross-linking of the polymer with the pendant phenolic group can affect the porosity of the interpenetrating polymer network and the size of the fibrin fibers, as the cross-linking of the polymer around the fibrin fibers will inhibit the growth of the fibrin fibers.

The polymer is therefore included in the reaction mixture at a concentration that is sufficient to provide a cross-linked polymer around the fibrin fibers. The reaction mixture may have any concentration of the polymer that is suitable to provide a hydrogel having the desired resultant cross-linked polymer network. A suitable concentration of polymer used may also depend on the degree of substitution of the pendant phenolic group in the polymer, as well as the concentration of enzyme used for cross-linking and the concentration of fibrin included in the reaction mixture. The suitable concentration of the polymer may also be dependent on the molecular weight of the polymer used. When the polymer has a higher molecular weight, the concentration may need to be lowered to achieve the desired hydrogel properties. In some embodiments, the polymer concentration may vary in the range of about 0.1 mg/ml to about 50 mg/ml, about 0.5 mg/ml to about 30 mg/ml, about 1 mg/ml to about 20 mg/ml, or about 2 mg/ml to about 10 mg/ml, or the polymer concentration may be about 0.1 mg/ml or greater, about 0.5 mg/ml or greater, about 1 mg/ml or greater, or about 2 mg/ml or greater.

Similarly, the degree of substitution of the phenol group on the polymer may affect the degree of cross-linking obtained in the hydrogel. The degree of substitution of the phenol group in the polymer is defined as the number of pendant phenolic groups per 100 monomeric units of the polymer. Thus, the degree of substitution of the phenol group may vary, such as from about 0.5 to about 50, from about 1 to about 30, from about 2 to about 20, from about 3 to about 10. In one embodiment, the degree of substitution may be about 5.

As indicated above, the reaction mixture contains a concentration of peroxidase that achieves the desired extent of cross-linking, taking into account the concentration of the various other components in the mixture which will influence the degree of cross-linking in the final hydrogel. For example, the reaction mixture may contain from about 0.005 unit/ml to about 5 unit/ml, from about 0.01 to about 2 unit/ml, from about 0.01 to about 0.5 unit/ml, about 0.005 unit/ml or greater, about 0.01 unit/ml or greater or about 0.1 unit/ml or greater of the peroxidase.

The amount of peroxide used will also affect the amount of cross-linking that occurs and thus will have an impact on the structure of the final hydrogel. The concentration of $H_2O_2$ added to the reaction mixture may be, for example, from about 1 µM to about 5000 µM, from about 5 µM to about 2000 from about 10 µM to about 1500 µM, from about 20 µM to about 1000 µM, or about 1 µM or greater, about 5 µM or greater, about 10 µM or greater, or about 20 µM or greater.

In addition to the effect of the cross-linking of the polymer around the fibrin fibers, the concentration of fibrinogen and the concentration of thrombin will influence the size of the fibrin fibers formed and thus also the porosity of the hydrogel. For example, fibrinogen may be included in a concentration from about 0.1 mg/ml to about 50 mg/ml, from about 0.5 mg/ml to about 25 mg/ml, from about 1 mg/ml to about 10 mg/ml, from about 2 mg/ml to about 5 mg/ml, about 0.1 mg/ml or greater, about 0.5 mg/ml or greater, about 1 mg/ml or greater, or about 2 mg/ml or greater. The thrombin may be included at a concentration from about 0.01 unit/ml to about 10.0 unit/ml, from about 0.05 unit/ml to about 5.0 unit/ml, from about 0.1 unit/ml to about 2.0 unit/ml, about 0.01 unit/ml or greater, about 0.05 unit/ml or greater, or about 0.1 unit/ml or greater.

The parameters affecting cross-linking and fibrin fiber formation can readily be adjusted to yield a hydrogel having the desired stiffness, softness and porosity. A skilled person can adjust such parameters and determine the affect of different combinations using routine laboratory work.

In a particular embodiment, the reaction mixture comprises hyaluronic acid-tyramine conjugate at a concentration of about 1 mg/ml to about 20 mg/ml, peroxidase at a concentration of about 0.01 unit/ml to about 0.5 unit/ml, hydrogen peroxide at a concentration of about 20 µM to about 1000 fibrinogen at a concentration of about 1 mg/ml to about 10 mg/ml, and thrombin at a concentration of about 0.1 unit/ml to about 2.0 unit/ml.

To increase the extent and rate of angiogenesis once the hydrogel is contacted with endothelial cells, it may be desirable to include one or more angiogenic proteins in the reaction mixture so that the angiogenic protein or proteins is included in the final hydrogel. Angiogenic proteins are known, and include for example, VEGF, FGF-2 and PDGF, as well as soluble forms of VEGFR, PDGFR and NRP-1.

Similarly, it may be desirable to include one or more other therapeutic agents in the reaction mixture for inclusion in the resultant hydrogel. The therapeutic agent may be any agent that has a biological, pharmacological or therapeutic effect in a body, and includes a protein, a nucleic acid, a small molecule or a drug. A therapeutic agent that is a protein may be a peptide, an antibody, a hormone, an enzyme, a growth factor, or a cytokine. A therapeutic agent that is a nucleic acid may be single stranded or double stranded DNA or RNA, a short hairpin RNA, an siRNA, or may comprise a gene encoding a therapeutic product.

Cells capable of undergoing angiogenesis may be may be included in the reaction mixture, thus seeding the resultant hydrogel with cells capable of undergoing angiogenesis. The cell may be any cell capable of undergoing angiogenesis, for example an endothelial cell including for example a vascular endothelial cell, for example a human umbilical vein endothelial cell (HUVEC). The cell may be a transformed cell or a tumor cell that has attained the ability to undergo angiogenesis. For example, the cells may be coated onto microbeads and included into the reaction mixture prior to gelling.

Where cells or other biological components are included as additives in the reaction mixture, it will appreciated that the conditions of the reaction mixture (buffer, pH, temperature, other components) should be chosen in order to maintain cell viability or the desired activity of any biological additive.

The reaction mixture is prepared so that the cross-linking and fibrin formation will occur together in the reaction mixture. Thus, the reaction mixture may be prepared to include all the components except for the peroxidase and the thrombin, which components may be added last, either to together or sequentially, in order to initiate the cross-linking and fibrinogen cleavage.

The reaction mixture may then be incubated, allowing for the enzymatic oxidative coupling of the phenol groups on the polymer to be cross-linked and for the fibrinogen to be processed into fibrin. As well, the incubation will allow for the hydrogel to gel. For example, upon mixing of all the components, the reaction mixture may be incubated for 5 minutes to an hour to achieve formation of the hydrogel. The incubation time will vary depending on the concentration of the various components included in the reaction mixture. Prior to gelation, the reaction mixture may be poured into a suitable mould in order to form a hydrogel having desired shape and dimensions.

If desired to be administered to a subject, the formed hydrogel may be implanted into a subject, for example, by surgical techniques. Alternatively, the reaction mixture may be implanted into a subject following mixing but before gelation, for example by injection of the reaction mixture at a desired site for angiogenesis in the subject.

If endothelial cells have been included in the reaction mixture, and the hydrogel is formed prior to implantation, prevascularization of the endothelial cells may be stimulated before the hydrogel is implanted in the subject, for example using surgical techniques to deliver the hydrogel to the desired site.

Thus, there is also provided a hydrogel, which may be formed in accordance with the above-described methods. The hydrogel comprises interpenetrating network of a cross-linked polymer and fibrin. The cross-linking of the polymer occurs via oxidative coupling between pendant phenolic groups on the polymer as a result of enzymatic oxidative coupling.

The hydrogels may be porous due to the inclusion of the fibrin. The fibrin fibers in the hydrogel provides a vehicle for migration of endothelial cells undergoing angiogenesis, as the endothelial cells can degrade the fibrin and migrate through the fibrin regions.

The hydrogels may also exhibit increased resistance to degradation during angiogenesis when used as a scaffold due to inclusion of the cross-linked polymer. The polymer surrounds the fibrin fibers, providing structural elements to the hydrogel that are not as susceptible to factors secreted by cells encapsulated within the gel.

The rate of degradation of the hydrogel may be measured, for example by exposing the hydrogel to a protease such as trypsin and then measuring weight loss of the hydrogel over time, for example as set out in Example 1 below. In some embodiments of the hydrogel, the hydrogel has a degradation rate of about 1% to about 20% weight loss per hour, measured by trypsin degradation of the gel upper surface when formed in a 1.5 ml eppendorf tube.

Depending on the polymer used, the hydrogel may be biocompatible, biodegradable and have low immunogenicity. If a biopolymer is used, for example hyaluronic acid or dextran, the polymer component of the hydrogel may slowly be degraded within the body of a subject by natural enzymes.

The hydrogel may have a desired stiffness and porosity as described above, based on the extent of cross-linking that occurs within the hydrogel and the size of the fibrin fibers that are formed in the hydrogel. Thus, mechanical properties of the hydrogel may be affected or controlled by adjusting the polymer concentration, fibrinogen concentration, enzyme concentration and/or enzyme cofactor concentration in the reaction mixture used to form the hydrogel.

The hydrogel may include one or more of an angiogenic protein, a therapeutic agent, and an endothelial cell capable of undergoing angiogenesis. These additional components may be added during formation of the hydrogel, or may be infused in or adhered to the hydrogel following formation of the hydrogel.

The hydrogels as described herein may used as a scaffold to support angiogenesis. Thus, there is provided a method of promoting angiogenesis. The method comprises contacting a population of cells capable of undergoing angiogenesis with the hydrogel as described herein under conditions sufficient for the population of cells to initiate angiogenesis.

Conditions sufficient for the population of cells to initiate angiogenesis will depend on a number of factors, including the cell type used. For in vitro methods, such conditions are standard techniques used in tissue culture, as will be appreciated by a skilled person. For in vivo methods, such conditions include placing the cell in a suitable in vivo environment for angiogenesis, as will be appreciated by a skilled person.

The hydrogel provides a structural scaffold that provides a suitable physical environment to promote or allow for the formation of cellular structures and organizations associated with angiogenesis, including the formation of sprouts, hollow tubes or intact blood vessels. As will be appreciated, angiogenesis is the process of developing new blood vessels from existing blood vessels, and includes the processes of migration of the cells that will from the vessel structure, reorganisation of the cells into structures and proliferation of the cells to form the vessels. Thus, reference to promoting angiogenesis includes promoting or providing conditions conducive to any stage or part of the angiogenesis process. Reference to undergoing angiogenesis includes a cell or population of cells undergoing any stage or part of angiogenesis.

The cells used in the method are any cells capable of undergoing angiogenesis. For example, the cells may be endothelial cells as described above. The cells may also be from a transformed cell line, a tumour cell line or an immortalized cell line that has the ability to undergo angiogenesis.

The cells may be encapsulated or embedded in the hydrogel, cultured on the hydrogel, or may be cells in vivo that are in contact with the hydrogel.

Thus, the method may be conducted in vitro using cultured cells or primary cells, or may be conducted in vivo, using cells such as primary cells, cells explanted from a subject, cells from an established cell line or cells that are in vivo in the subject in which the method is conducted.

If the method is performed in vitro, the cells are cultured using standard tissue culture techniques for the appropriate cell type used, for example using appropriate growth medium, temperature, atmosphere and other growth conditions that allow for growth of the cells in culture.

If the method is performed as an in vivo method, the hydrogels may be pre-formed and then implanted into a subject. Alternatively, the hydrogels may be formed in situ by injection of the reaction mixture containing the hydrogel precursor prior to gelling of the hydrogel. It has been experimentally confirmed that the enzyme-mediated oxidation and cross-linking process does not involve significant cytotoxicity and does not cause substantial loss of protein activity. Moreover, the rate of hydrogel formation can be conveniently affected or controlled by adjusting the various concentrations of the components of the reaction mixture and can be fast enough to prevent uncontrolled diffusion of bioactive agents to surrounding tissues before the hydrogel is formed.

Thus, the cell may be a cell located in a subject in need of angiogenesis. For example, the cell may be a cell within a subject having a disorder which may be treated with angiogenesis or a subject requiring angiogenic treatment. In some embodiments, the subject is a human subject. For example, the subject may be in need of treatment of, or prevention of, diabetic retinopathy or gangrene.

As indicated above, cells may be included in the hydrogel, and one or more angiogenic proteins, and/or one or more therapeutic agents may also be included.

The hydrogel is also suited for use as a support for cell growth, not just for angiogenesis. For example, the hydrogel may be used a physical substrate for cells seeded on the surface but which may not be cells that undergo angiogenesis, for example fibroblasts. The hydrogel can also be used as a soft tissue engineering scaffold.

Hydrogels with different mechanical properties may be conveniently formed and used for cell cultivation/differentiation in two-dimensions (2D) or three-dimensions (3D), and for effective regeneration of tissue.

Thus, the hydrogel may be used in a method of growing or differentiating cells on or in a hydrogel. There is provided a method of culturing a cell, including growing a cell, including differentiating a cell. The method comprises contacting a cell with the hydrogel as described herein under conditions sufficient for the cell to grow. Growing includes proliferation and differentiation, as well as maintaining a static state such as senescence.

The cells may be dispersed in the reaction mixture if the cells are to be encapsulated within the hydrogel. Alternatively, the cells may be seeded on the surface of the hydrogel.

Culture conditions sufficient for growing the cell will depend on a number of factors, including the cell type used. Such conditions are standard techniques used in tissue culture, as will be appreciated by a skilled person. Thus, the cells are cultured using conventional tissue culture techniques, including suitable growth medium and growth conditions as required by the cells and in keeping with the particular application for which the cells are being grown on or in the hydrogel. Such tissue culture techniques and requirements for particular cell types will be known by a person of ordinary skill.

The hydrogels as described herein are thus suitable for many biological applications due to the biodegradability and biocompatibility of components used to form the hydrogels. For example, the hydrogels may be combined with cells to form artificial tissues.

The methods, hydrogels and uses as described herein are further exemplified by way of the following non-limiting examples.

EXAMPLES

Example 1

Throughout this example, the following abbreviations are used. DMEM: Dulbecco's Modified Eagle Medium; EGM-2: Endothelial Cell Basal Media-2; FBS: fetal bovine serum; HAT or HA-Tyr: hyaluronic acid-tyramine conjugate; HFF1: human foreskin fibroblast; HRP: horse-radish peroxidase; HUVEC: human umbilical vein endothelial cells; PBS: phosphate buffered saline; PI: propidium iodide.

Materials and Methods

Materials.

HA (90 KDa) was kindly donated by Chisso Corporation (Tokyo, Japan). Diethoxyethyl amine (DA), N-hydroxysuccinimide (NHS), 1-ethyl-3-(3-dimethylaminopropyl)-carbodiimide hydrochloride (EDC), tyramine hydrochloride, bovine plasma fibrinogen and bovine thrombin were from Sigma (Singapore). Horeseradish peroxidase was purchased from was from Wako Pure Chemical Industries (Japan). HUVEC and EGM-2 bullet kits were purchased from Lonza (Singapore). Cytodex 3 microcarrier beads were purchased from GE Healthcare.

Synthesis of HA-Tyr Conjugates.

HA-Tyr conjugates were synthesized as described previously (Lee et al., 2008).

Characterization of HAT-Fibrin Gels.

Using the absorbance method described earlier, the relationship between different gel compositions and the structure of fibrin fiber network was investigated. Experiments carried out for the characterization of HAT-fibrin gels were done at pH 7.6. The gels were formed by mixing HAT (2.5 mg/ml), fibrinogen (2.5 mg/ml), thrombin (0.24 unit/ml), HRP (0.062 unit/ml), and $H_2O_2$ (6250 μM) in phosphate buffer (0.277M). These gels were incubated at 37° C. for 30 minutes in an orbital shaker, and the absorbance was subsequently measured at 350 nm using the plate reader.

The same method was used to determine the effect of varying $H_2O_2$ concentrations on the structure of fibrin network in the gel. HAT-fibrin gels were polymerized using the materials described above and a varying concentration of $H_2O_2$ ranging from 0 μM to 6250 μM was used. Gel absorbance was measured 30 minutes later.

The absorbance method was also used to investigate the optimal $H_2O_2$ concentration that is able to give a gel with maximum mechanical strength. HAT gels at pH 7.6 were made by mixing HAT (2.5 mg/ml), $H_2O_2$ ranging from 0 μM to 6250 μM, 0.9% NaCl, and HRP (0.062 unit/ml) in phosphate buffer (0.277 M). Absorbance of the gels was measured at 312 nm. Gel compositions and their specific definitions are stated in Table 1. FIG. 1 is a schematic depiction of formation of the four types of gel compositions shown in Table 1.

Gel Degradation Assay.

The degradation of the interpenetrating hydrogel networks was determined by weight loss measurement. 330 μl of gel precursors containing HA-Tyr (5 mg/ml), $H_2O_2$ (0, 24, 49 and 195 μM), fibrinogen (2.5 mg/ml), thrombin (0.24 unit/ml) and HRP (0.062 unit/ml) were added to 1.5 ml eppendorf tubes and mixed evenly. The hydrogel was allowed to cross-link at 37° C. for 1 h. Then 350 μl of 0.01% trypsin was added to the top of the gels to start the degradation process. Every hour for the next nine hours the trypsin was removed by pipetting, and the tubes were weighed to obtain the weight of gel. Then 350 μl of 0.01% fresh trypsin was added to continue the degradation process until the fibrin gel was fully degraded. Rate of degradation for each gel composition was determined via percentage of weight loss over time.

Cell Culture.

Human umbilical vein endothelial cells (HUVECs, Lonza, USA) were cultured in endothelial cell basal media-2 (EGM-2, Lonza, Wakersville Md., USA) that was supplemented with human endothelial growth factor (hEGF), hydrocortisone, GA-1000 (Gentamicin, Amphotericin B), fetal bovine serum (FBS), vascular endothelial growth factor (VEGF), human fibroblast growth factor (hFGF-B), heparin, R3-IGF-1, and ascorbic acid. HUVECs between passages 3 and 4 were used for the coating of beads.

Human foreskin fibroblast (hFF1) for long term culture of blood vessels were cultured in Dulbecco's Modified Eagle Medium (DMEM, Gibco, USA) containing 15% Fetal Bovine Serum (FBS), and 1% penicillin/streptomycin.

Both cell types were cultured in T75 flasks (Nunc, Denmark) and incubated at 37° C. in 5% $CO_2$ atmosphere. Fresh medium was replaced every 2-3 days and the culture was maintained at approximately 90% confluency.

In Vitro Angiogenesis Studies.

HUVECs (passage number 3 and 4 were used) were cultured using EGM-2 medium following the manufacturer's protocol. Coating of the microcarrier beads was performed by modifying a previously established protocol (Nakatsu et al., 2007). Briefly, 2 ml of HUVEC at 800,000 cells/ml was mixed with approximately 6000 cytodex beads in a FACS tube. The FACS tube was incubated at 37° C. and 5% $CO_2$ and shaken every 20 mm for 4 h to allow cell adhesion. Next, the beads were transferred to a T25 flask supplemented with 5 ml of EGM-2, and incubated for another 24 hours at 37° C. and 5% $CO_2$. The following day, the beads were transferred to a 50 ml tube and resuspended to 370 beads/ml in PBS. Gel precursors containing the cell-coated microcarriers, fibrinogen (5 mg/ml), HA-Tyr (5.45 mg/ml) and $H_2O_2$ (0 µM to 1.95 µM) were cross-linked by adding the enzymes, 0.24 unit/ml thrombin and 0.062 unit/ml HRP. 330 µl of the mixture was then transferred to each well of a 48 well plate. Approximately 50 beads were in each well. The plate was incubated for 1 h at 37° C. and 5% $CO_2$ to allow gel formation. 0.5 ml of EGM-2 was then added on top of the gels and the plate was returned to the incubator. Replacement of fresh medium was done every other day. The gels were monitored over a time period of 7 days.

Live Dead Staining of HUVEC Beads.

Live dead staining was performed on HUVECs coated on cytodex beads encapsulated in gels. 4 µL of calcein AM (2 µL/ml, Invitrogen, USA) and 2 µL of propidium iodide (1 µL/ml, SIGMA, Germany) were added to 2 ml of PBS. 300 µL of this staining solution was added on top of the gels in each well of the 48 well plate. The plate was then incubated for 45 minutes at 37° C. and 5% $CO_2$. Living cells were stained bright green, while dead cells were stained red. This was visualized using a fluorescence microscope (Olympus, USA), and observation was done at 1 hour, day 1, and day 7 after the gels were formed.

Quantification of Vessels.

Images of the beads were captured on a bright field microscope (Olympus, USA) at 10× magnification on days 3 and 6 after gel formation. A total of at least 10 beads were analyzed for each gel composition. The number of sprouts per beads and length of individual sprout were determined by manual counting and measurement, and then averaged.

Long Term Culture of HUVEC Coated Beads.

Beads were coated with HUVEC and encapsulated in gels made using the same concentration of materials as described above under "In vitro angiogenesis studies". After 1 h of incubation, fibroblasts at a cell density of 10000 cells/ml were seeded on top the gels. Fresh EGM-2 was replaced every other day. These gels were monitored over a period of 21 days. Bright field images of the vessels were taken at day 7, day 14, and day 21.

Results

Four $H_2O_2$ concentrations (24.4 µM, 48.8 µM, 97.6 µM, and 195 µM) were selected to test for rate of degradation.

Figure 3:
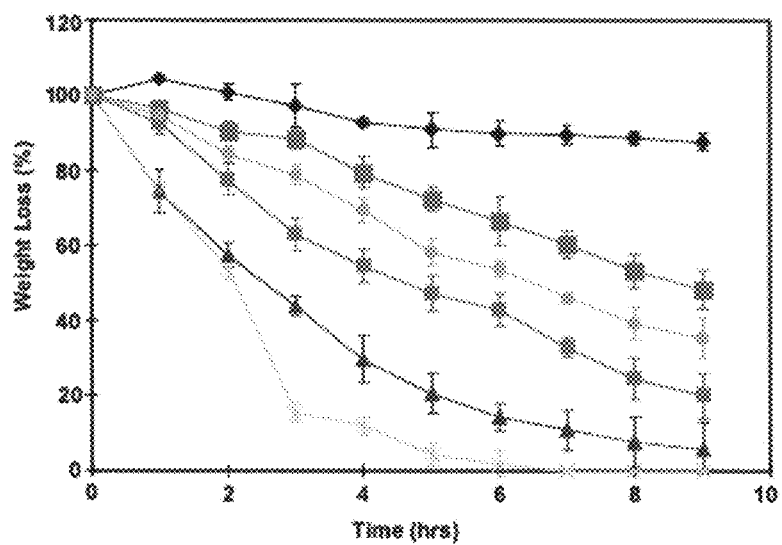
FIG. 3. Degradation of gels in the presence of 0.0125% of trypsin, as measured by the amount of weight loss. Concentrations of $H_2O_2$ used-(—■—): 24.4 µM, (—●—): 48.8 µM, (—■—): 97.6 µM, (—♦—): 195 µM, (—▲—): Fibrin Gel, (—✱—): Fibrin Gel+HAT conjugates.

FIG. 3 shows that over a time period of 9 hours, the weight of all the gels decreased when incubated with trypsin. However, the HAT-fibrin gels were the most resistant to degradation, as compared to the fibrin gel and the fibrin gel containing HAT conjugates. Fibrin gel took a longer time than fibrin gel containing HAT to degrade. As observed, HAT-fibrin gel made using 195 µM of $H_2O_2$ was more resistant to degradation than that those formed using the other $H_2O_2$ concentrations, determined by its relatively low percentage of weight loss over time. Thus, the higher the $H_2O_2$ concentration used in HAT-fibrin gel formation, the lower its weight loss with time.

Short-Term Culture of HUVEC Coated Cytodex-3 Beads.

HUVECs were cultured to about 95% confluency before they were used for the coating of cytodex-3 beads. Beads that were fully coated appeared to have an uneven surface, while those that were partially coated with cells had a smooth surface.

Figure 4:
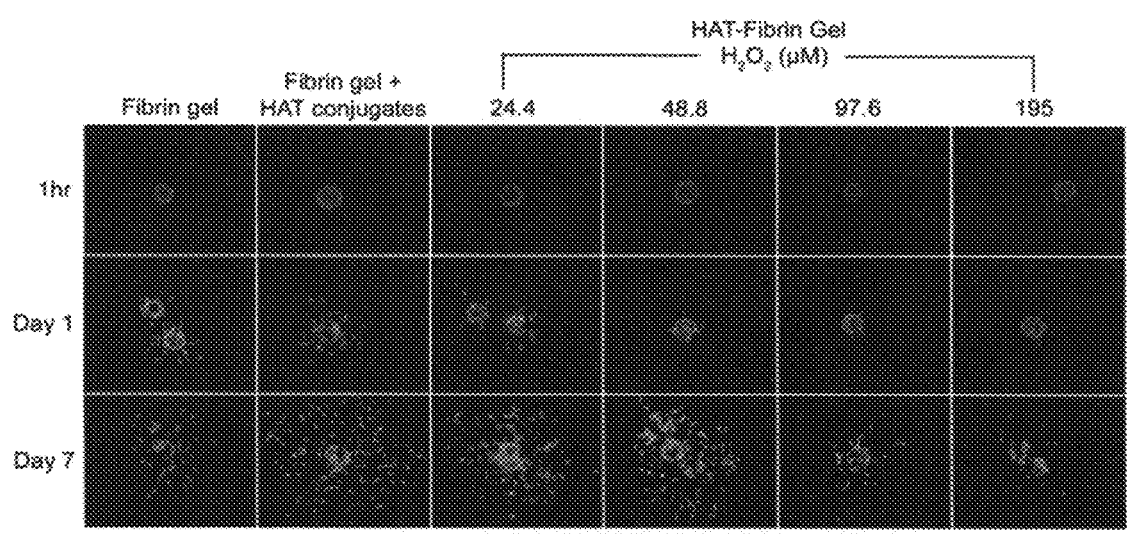
FIG. 4. Live/Dead Staining of HUVEC coated beads. Cells coated on the surface of cytodex-3 beads were still alive at the end of 1 week culture period, as observed by the bright fluorescent green staining.

Live dead staining assay was performed on HUVEC coated beads that were embedded in gels formed using the selected $H_2O_2$ concentrations. Controls included fibrin gel and fibrin gel containing HAT conjugates. When viewed using the fluorescence microscope, bright green staining of the cells was observed at the specified time points (FIG. 4). Very few cells were stained red (data not shown), indicating that a majority of the cells still remained alive.

It can be observed from the fluorescent images that the extent of cell proliferation increased with time. More importantly, the magnitude of cell proliferation seemed to be comparable between fibrin gel containing HAT conjugates and HAT-fibrin gels formed using $H_2O_2$ concentrations: 24.4 µM and 48.8 µM. As the concentration of $H_2O_2$ increased from 97.6 µM to 195 µM, the number of cells invading into the gels decreased, as depicted by the decreased amount of bright green staining. To identify the extent of sprout formation among the gels of different compositions, bright field images of the beads were taken on days 3 and 6 of incubation (FIG. 5).

Figure 5:
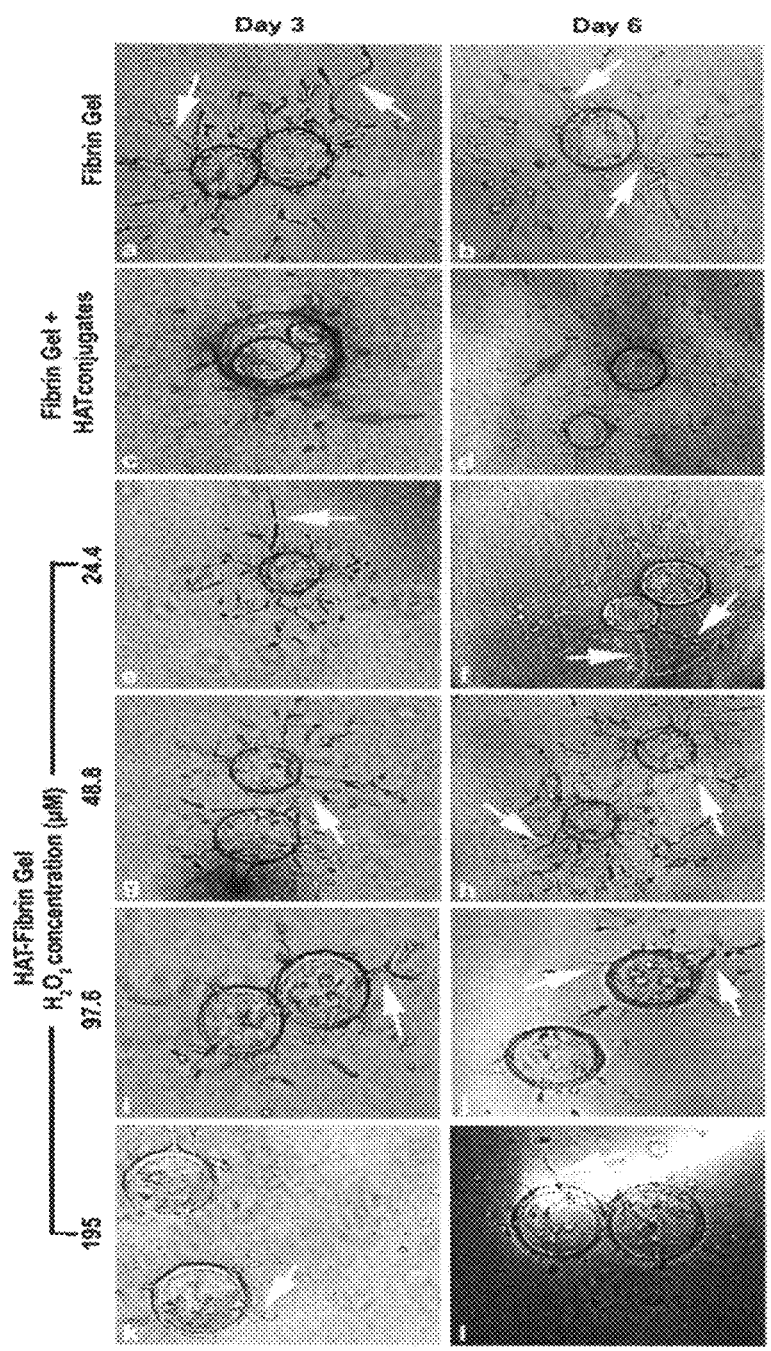
FIG. 5. Bright field images of HUVEC coated beads encapsulated in gels of different compositions and $H_2O_2$ concentrations (a,c,e,g,i,k: Day 3 of incubation), (b,d,f,h,j,l: Day 6 of incubation). Sprouts refer to thin extensions made up of HUVECs that move away from the beads (white arrows). Migratory cells refer round cells that invade the gel matrix. Extensive sprouting was observed in gels made with 24.4 µM and 48.8 µM of $H_2O_2$ on both days 3 and 6. Migratory cells were most prominent in fibrin gels containing HAT conjugates.

FIG. 5 shows no obvious difference in the extent of sprouting between fibrin gel and gels formed with 24.4 µM and 48.8 µM of $H_2O_2$ on day 3. However, on day 6, gels made using these two concentrations of $H_2O_2$ resulted in extensive sprouting that invaded into the gel matrix. In contrast, there wasn't any significant increase in sprouts observed in fibrin gels on day 6. Instead, more migratory cells were seen. HAT-fibrin gels formed with $H_2O_2$ concentrations higher than 48.8 µM had very few and short sprouts on both days of incubation. Sprout formation wasn't evident in fibrin gel containing HAT conjugates.

Figure 6:
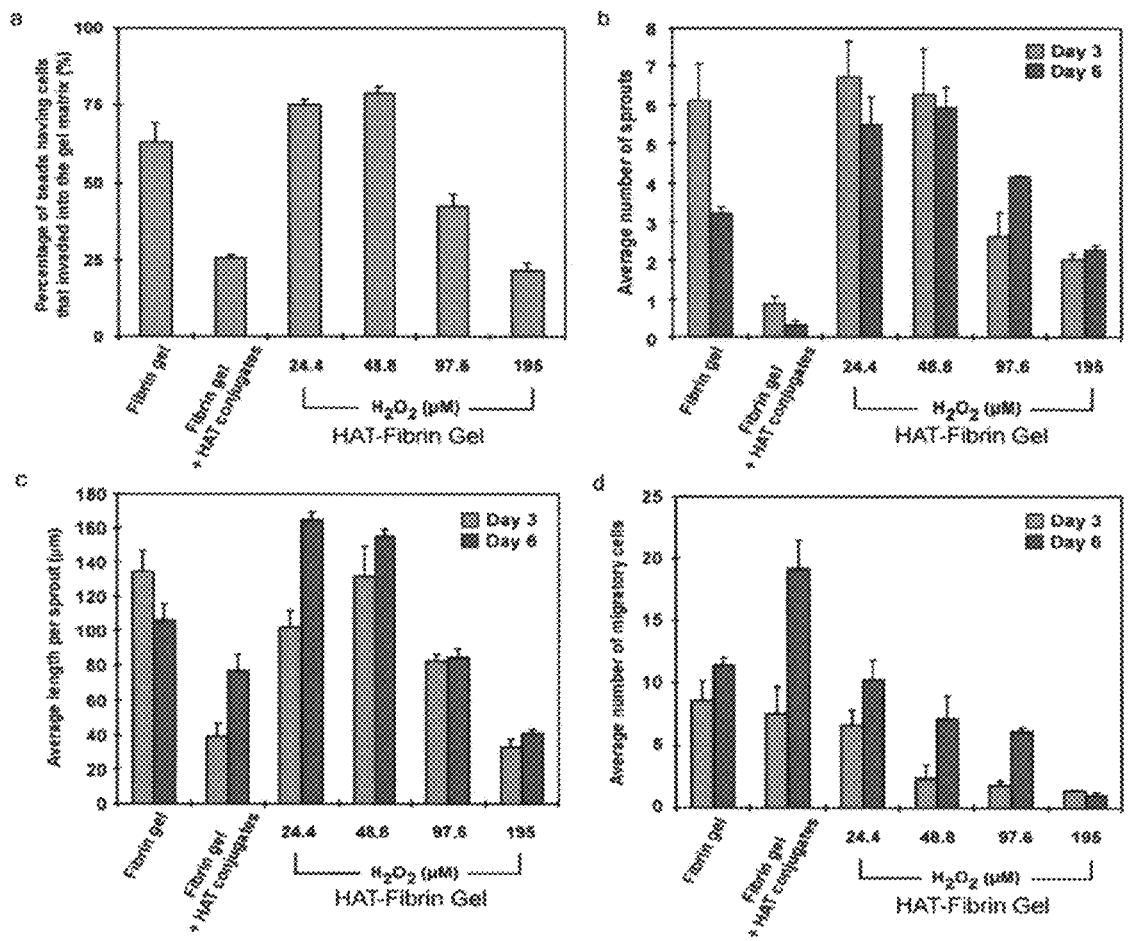
FIG. 6. In vitro quantification of sprouts with varying concentrations of $H_2O_2$. (a) A bar graph depicting percentage of beads with cells invading into the gel against increasing concentration of $H_2O_2$ was plotted. (b) Bar graph illustrating the effect of $H_2O_2$ concentration on the average number of sprouts formed per bead on days 3 and 6 of incubation. (c) Bar graph illustrating the effect of $H_2O_2$ concentration on the average length per sprout on days 3 and 6 of incubation. (d) Bar graph illustrating the effect of $H_2O_2$ concentration on the average number of migratory cells formed on days 3 and 6 of incubation.

From these images, it was inferred that both $H_2O_2$ concentrations: 24.4 µM and 48.8 µM gave rise to a gel structure that allowed for optimal cell adaptation and proliferation, in the gel compositions tested in this study. To confirm this, quantification studies were conducted (FIG. 6).

Effect of Varying $H_2O_2$ Concentrations on HUVEC Sprout Formation.

Day 1 after gel formation, the number of beads in each well which contained cells that invaded the gel was tabulated as a percentage of the total number of beads in that particular well. FIG. 6a shows that polymerization of HAT-fibrin gels using 24.4 µM or 48.8 µM of $H_2O_2$ resulted in the greatest percentage of HUVEC coated beads that invaded the gel. In contrast, gels formed using a $H_2O_2$ concentration of 97.6 µM and above resulted in lesser than 50% of beads with cells that invaded the gel. To affirm this observation, the beads were cultured for one week and further quantification was done on days 3 and 6 (FIGS. 6b-d).

The total number of sprouts on at least 10 beads was counted, and average number of sprouts per bead was determined. FIG. 6b shows that on both days 3 and 6, there was a general trend of decreasing sprout number with increasing concentrations of $H_2O_2$. Fibrin gel containing HAT conjugates had the lowest number of sprouts on both days of quantification. On the contrary, fibrin gel alone had about the same number of sprouts as that formed with the lowest $H_2O_2$ concentration on day 3, which decreased to half of the original amount on day 6.

On day 3, HAT-fibrin gel formed using 24.4 µM of $H_2O_2$ resulted in a gel structure that stimulated the formation of the most number of sprouts per bead. However, on day 6, the average number of sprouts was the highest in a gel formed with 48.8 µM of $H_2O_2$. Based on this result, 24.4 µM and 48.8 µM seemed to be the most desirable $H_2O_2$ concentrations.

Consistent with this trend, the average length of sprout decreased with increasing concentrations of $H_2O_2$ on both days (FIG. 6c). The length of each sprout was the longest for HUVEC coated beads embedded in gels formed using 24.4 µM and 48.8 µM of $H_2O_2$. The average number of migratory cells per bead in each well was also quantified. FIG. 6d shows that there was an overall increase in the number of migratory cells on day 6, as compared to day 3. In addition, on both days 3 and 6, there was a general trend of decreasing migratory cell number as the concentration of $H_2O_2$ increased from 24.4 µM to 195 µM.

Long-Term Culture of HUVEC Coated Cytodex-3 Beads with Fibroblasts.

Figure 7:
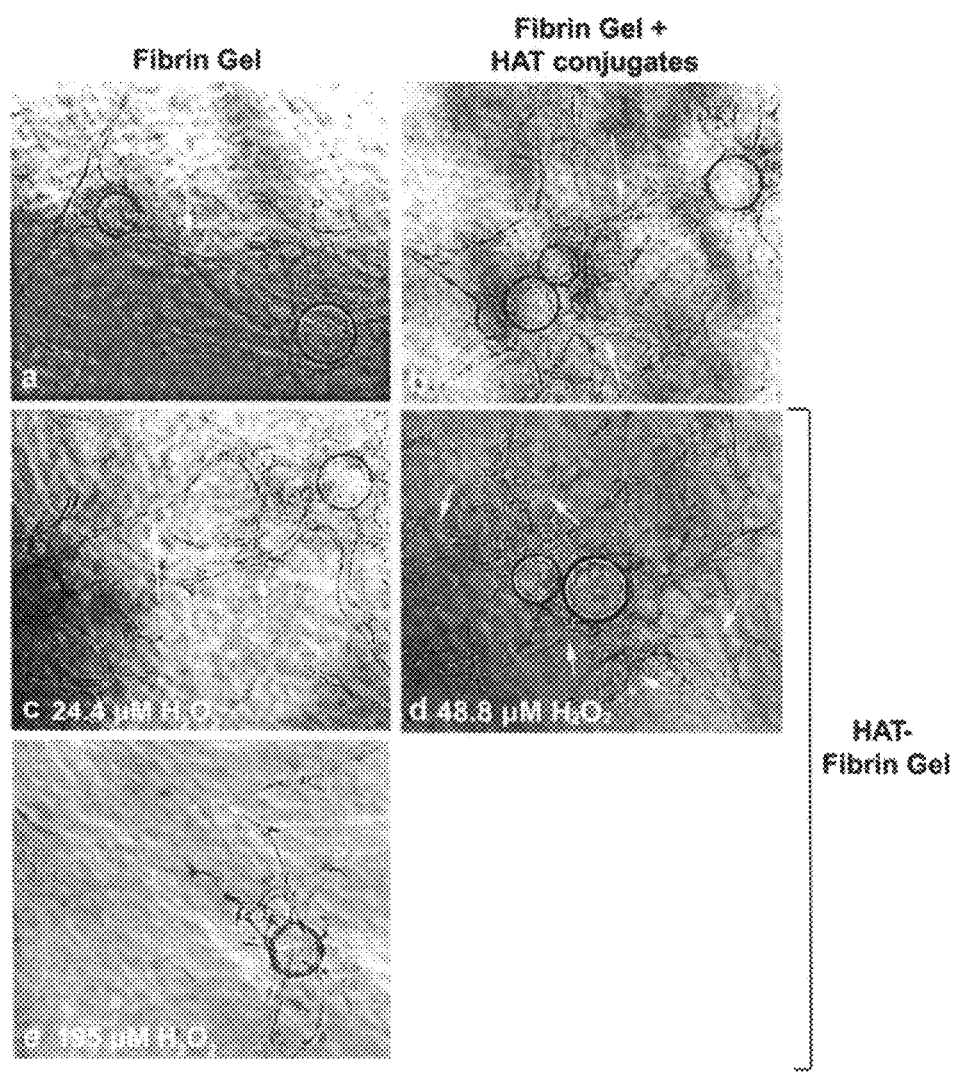
FIG. 7. Bright field images of HUVEC coated beads encapsulated in gels of different compositions and $H_2O_2$ concentrations on day 21. Fibroblasts were seeded on top of the gels to support hollow tube formation. Vessels refer to hollow tubes made up of HUVECs that extend into the gel matrix (white arrows). Anastomosis was evident in some of the gels (white circle). Sprouts that appear thin and long were present in every gel composition (purple arrows). Extensive extensions were seen to invade into the gel made with 24.4 µM and 48.8 µM of $H_2O_2$. Migratory cells were most prominent in fibrin gel+hyaluronic acid-tyramine (HAT) conjugates.

Over 3 weeks of incubation, there was a notable difference in the extent of hollow vessel formation in gels made of different compositions and concentrations of $H_2O_2$. FIG. 7 shows the presence of hollow vessels and sprouts formed in various gel compositions. Hollow tubes are distinct from sprouts observed in FIG. 5 as they appear to be thicker. Hollow tube and sprout formation seemed to be the most extensive in gels formed using 48.8 µM of $H_2O_2$. In contrast, such tubes weren't as evident in gels formed with 195 µM of $H_2O_2$; instead, long, thin sprouts were seen. Presence of migratory cells was discernible in fibrin gels and fibrin gel containing HAT conjugates on day 7 (data not shown). In addition, anastomosis was seen in fibrin gel and HAT-fibrin gels made with 24.4 µM of $H_2O_2$. Furthermore, by day 21, the fibroblasts have infiltrated into some of the gels, namely, HAT-fibrin gels made with 24.4 µM of $H_2O_2$, fibrin gel with HAT conjugates, and fibrin gels (data not shown).

Figure 8:
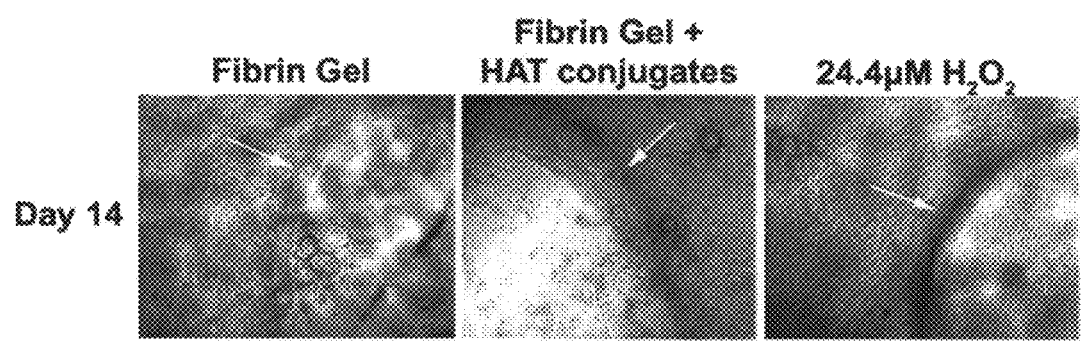
FIG. 8. Gels that showed signs of shrinking on day 14 of incubation. White arrows indicate the portions of the gel that have shrunk.

By day 14, HAT-fibrin gels formed using 24.4 µM of $H_2O_2$, fibrin gels with HAT conjugates, fibrin gel, and fibrin gel with aprotinin showed signs of shrinking (FIG. 8). This is determined by an observed retraction of the gel matrix.

Discussion

Figure 2:
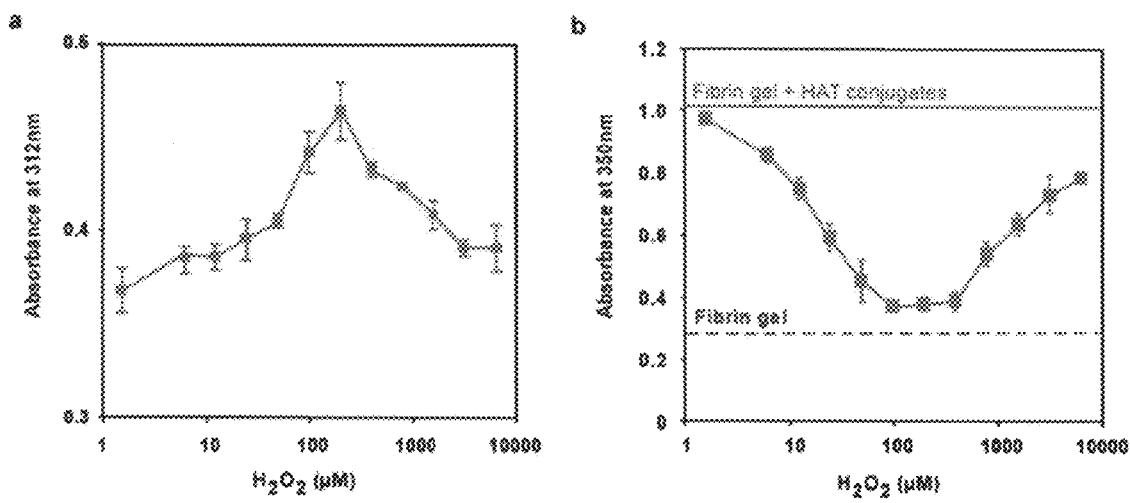
FIG. 2. Concentration of $H_2O_2$ affects the mechanical strength and structure of gel. (a) 195 µM of $H_2O_2$ was identified as the concentration that provided a HAT gel with maximal absorbance at 312 nm. (b) The $H_2O_2$ concentration that gave the highest absorbance value at 312 nm had the lowest absorbance at 350 nm.

Previously, it has been possible to improve strength of an HA gel by optimizing of $H_2O_2$ (Fan Lee et al., 2008). In the interpenetrating network gels prepared here, it was found that HAT-gel absorbance at 312 nm did vary with the concentration of $H_2O_2$ (FIG. 2a).

The structure of HAT-fibrin gels varies with $H_2O_2$ concentrations. Decreasing gel absorbance was observed with increasing concentrations of $H_2O_2$ (FIG. 2b). At lower $H_2O_2$ concentrations, less cross-linking of HAT occurred, which may allow for more aggregation of fibrin fibers, resulting in high gel turbidity and absorbance. More extensive aggregation of fibrin fibers may also result in larger pores within the gel.

To optimize a gel composition suitable for stimulating vessel formation, there is a need to compromise between gel stiffness and gel structure. Based on this, four different $H_2O_2$ concentrations that form gels of different mechanical strengths were tested for their rate of degradability. As expected, degradation rate increased with decreasing $H_2O_2$ concentrations (FIG. 4).

Cells respond differently to the physical properties of the surrounding matrix in which they are embedded. HAT-fibrin gels formed using the selected $H_2O_2$ concentrations resulted in different sprout formation efficiency. Extensive sprouting observed in gels formed using 48.8 µM of $H_2O_2$ may be due to gel stiffness, pore size, and thickness of fibrin fiber strands being more conducive for cells to self arrange into sprouts than the other concentrations of $H_2O_2$ tested (FIG. 5, 6b).

The percentage of beads with cells that invaded into the gel matrix on day 1, average number of sprouts, and average length of sprout on day 6 were similar in gels polymerized with 24.4 µM and 48.8 µM of $H_2O_2$ (FIG. 6a,c,d). As mentioned above, these $H_2O_2$ concentrations were able to create a physical environment that is conducive for sprout formation. Interestingly, a drop in the number of sprouts on day 6 was observed in gels formed using these $H_2O_2$ concentrations. This could be due to the disintegration of sprouts into migratory cells, as observed by a consequent increase in migratory cell number on day 6. Fibrin gel containing HAT conjugates gave the most number of migratory cells because the thick fibrin fibers are better in resisting traction forces exerted by the cells during movement within the matrix, leading to more efficient migration.

Long-term culture of the HUVEC coated beads proved the sprouts formed initially would eventually develop into hollow vessels that exist as thick tubes. This is due to growth factors that are secreted by fibroblasts that help in stabilizing the vascular network, preventing them from dissociating into single cells that migrate into the matrix (Tille and Pepper, 2002). The hollow vessels observed (FIG. 7) were empty lumens surrounded by many single polarized HUVECs (Fournier and Doillon, 1992). During the process of vessel formation, endothelial cells located at the distal end of the sprout are in their mitotic phase; hence, they divide and invade the gel matrix. In contrast, endothelial cells at the proximal end of the sprout will shorten and transit from an elongated to a round morphology, resulting in the formation of a lumen (Ingber and Folkman, 1989).

Consistent with the trend observed for short-term culture of HUVEC coated beads, gels made using 24.4 µM and 48.8 µM of $H_2O_2$ gave the most extensive formation of hollow vessels. As mentioned previously, this is due to the ability of these $H_2O_2$ concentrations in forming a gel with ideal physical properties that is most suitable for manipulation by the cells, enabling them to proliferate, migrate, arrange into sprouts, and further transit into a hollow lumen structure.

Infiltration of fibroblasts into the matrix of fibrin gels, fibrin gel with HAT conjugates, and HAT-fibrin gel made with 24.4 µM $H_2O_2$ is because these gels are too weak, hence, easily overcome by the proteolytic activity of proteases secreted by the fibroblasts as they migrate. Similar to the conclusions drawn from the gel degradation assay, these gels have been proven to be weaker than HAT-fibrin gels formed with a higher $H_2O_2$ concentration. Besides, this point is further proven by the retraction of gels observed in these gels at day 14 of incubation (FIG. 8). Shrinking of gels could be attributed to the cell traction forces exerted by both the fibroblast cells seeded on top of the gel and the HUVECs encapsulated within the gel. Cell traction forces are tensile forces generated by the cells that exert a pulling effect on the matrix. Since HAT-fibrin gels made with 24.4 µM of $H_2O_2$ was unable to withstand the effect of cell traction forces, we conclude that HAT-fibrin gels formed using 48.8 µM $H_2O_2$ is the optimized gel composition proven to support vessel formation, and is a potential scaffold for stimulating angiogenesis.

Hydrogels with interpenetrating polymer networks composed of hyaluronic acid-tyramine conjugate (HA-Tyr) and fibrin were formed using the oxidative coupling of phenol moieties catalyzed by hydrogen peroxide ($H_2O_2$) and horseradish peroxidase (HRP). Microcarrier beads coated with human umbilical vein endothelial cells (HUVEC) were successfully embedded in the hydrogels. Utilizing this catalytic system, it was possible to control the rate of hydrogel degradation by varying $H_2O_2$ concentration, which determined the hydrogel stiffness. Also, it was observed that encapsulation of HUVEC-coated beads in the hydrogels formed using different $H_2O$ concentrations resulted in varying degrees of sprouting into the hydrogel matrix, and varying abilities in supporting the formation of hollow vessels.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Similarly, the terms "include", "including", "includes" and other forms of these terms are intended in the non-limiting inclusive sense, that is, to include particular recited elements or components without excluding any other element or component. As used in this specification and the appended claims, all ranges or lists as given are intended to convey any intermediate value or range or any sublist contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

Ahmed, T. A. E., E. V. Dare, and M. Hincke, 2008. Tissue Engineering Part B reviews 14(2), 199-215.

Aper T., Schmidt A., Duchrow M., Bruch H.-P., 2006. Autologous Blood Vessels Engineered from Peripheral Blood Sample. European Journal of Vascular and Endovascular Surgery 33(1), 33-39.

Annemie Collen, Pieter Koolwijk, Marielle Kroon, Victor W. M. van Hinsbergh, 1998. Influence of fibrin structure on the formatuin and maintenance of capillary-like tubules by human microvascular endothelial cells. Angiogenesis 2, 153-165.

A. Stephanou, G. Meskaoui, B. Vailhe, P. Tracqui, 2006. The rigidity in fibrin gels as a contributing factor to the dynamics of in vitro vascular cord formation. Microvascular research 73, 182-190.

Bauters C, Asahara T, Zheng L P, Takeshita S, Bunting S, Ferrara N, Symes J F, Isner J M (1994) Site-specific therapeutic angiogenesis after systemic administration of vascular endothelial growth factor. J Vasc Surg 21, 314-325.

Baffour R, Berman J, Garb J L, Rhee S W, Kaufman J, Friedmann P (1992) Enhanced angiogenesis and growth of collaterals by in vivo administration of recombinant basic fibroblast growth factor in a rabbit model of acute lower limb ischemia: dose-response effect of basic fibroblast growth factor. J Vasc Surg 19, 181-191.

Bensaïd W, Triffitt J T, Blanchat C, Oudina K, Sedel L, Petite H., 2003. A biodegradable fibrin scaffold for mesenchymal stem cell transplantation. Biomaterials 24, 2497-2502.

Bruno Vailhé, Marc Lecomte, Nicolas Wiernsperger, Léone Tranqui, 2004. The formation of tubular structures by endothelial cells is under the control of fibrinolysis and mechanical factors. Angiogenesis 2(4), 331-344.

Cholewinski, E., et al., Tranexamic acid—an alternative to aprotinin in fibrin-based cardiovascular tissue engineering. Tissue Eng Part A., 2009. 15(11): 3645-53.

Chen, W. J. J., Abatangelo, G., 1999. Functions of Hyaluronan in wound repair. Wound Repair Regen. 7, 79-89.

Deed, R., Rooney, P., Kumar, P., Norton, J. D, Smith, J., Freemont, A. J., Kumar, S., 1997. Early respinse gene signaling is induced by angiogenic oligosaccharides of hyaluronan in endothelial cells. Inhibition by non-angiogenic, high molecular weight hyaluronan. Int. J. Cancer 71, 116-122.

Edward A. Phelps, Natalia Landazuri, Peter M. Thule, W. Robery Taylor, Andres J. Garcia, 2010. Bioartificial matrices for therapeutic vascularization. PNAS 107, 3323-3328.

Erin L. Pardue, Samir Ibrahim, Anand Ramamurthi, 2008. Role of hyaluronan in angiogenesis and its utility to angiogenic tissue engineering. Organogenesis 4(4), 203-214.

Fan Lee, Joo Eun Chung, Motoichi Kurisawa, 2008. An injectable enzymatically cross-linked hyaluronic-acid-tyramine hydrogel system with independent tuning of mechanical strength and gelation rate. Soft Matter 4, 880-887.

Fournier, N., Doillon, C. J., 1992. In vitro angiogenesis in fibrin matrices containing fibronectin or hyaluronic acid. Cell biology international reports 16, 1251-1263.

Fraser, J. R. E., Laurent, T. C., Laurent, U. B. G., 1997. Hyaluronan: its nature, distribution, functions and turnover. J. Intern. Med. 242, 27-33.

Furst, W., Banerjee, A., Redl, H., 2007. Comparison of structure, strength and cytocompatibility of a fibrin matrix supplemented either with tranexamic acid or aprotinin. J Biomed Mater Res B Appl Biomater. 82(1):109-14.

Jockenhoevel S, Chalabi K, Sachweh J S, Groesdonk H V, Demircan L, Grossmann M, Zund G, Messmer B J., 2001. Tissue engineering: complete autologous valve conduit—a new moulding technique. Thorac Cardiovasc Surg, 49 (5). 287-290.

Lukas Urech, Anne Greet Bitterman, Jeffrey A. Hubbell, Heike Hall, 2004. Mechanical properties, proteolytic degradability and biological modifications affect angiogenic process extension into native and modified fibrin matrices in vitro. Biomaterials 26, 1369-1379.

Martin N. Nakatsu, Richard C. A. Sainson, Jason N. Aoto, Kevin L. Taylor, Mark Aitkenhead, Sofia Oerez-del-Pulgar, Philip M. Carpenter, Christopher C. W. Hughes, 2003. Angiogenic sprouting and capillary lumen formation modeled by human umbilical vein endothelial cells (HUVEC) in fibrin gels: the role of fibroblasts and angiopoietin-1. Microvascular Research 66, 102-112.

Montassano, R., Kumar, S., Orci, L., Pepper, M. S., 1996. Synergistic effect of hyaluronan oligosaccharides and vascular endothelial growth factor on angiogenesis in vitro. Lab. Invest. 75, 249-262.

Nakatsu, M N., I. Davis, and C C, Hughes, Optimized fibrin gel bead assay for the study of angiogenesis. J Vis Exp, 2007(3): 186.

Nehls, V. and D. Drenckhahn, A microcarrier-based cocultivation system for the investigation of factors and cells involved in angiogenesis in three-dimensional fibrin matrices in vitro. Histochem Cell Biol, 1995. 104(6): 459-66.

Pankajakshan, D., V. K. Krishnan, and L. K. Krislman, Vascular tissue generation in response to signaling molecules integrated with a novel poly(epsilon caprolactone)-fibrin hybrid scaffold. J Tissue Eng Regen Med, 2007. 1(5): 389-97.

Perumal Thiagarajan, Amy J. Rippon, David H. Farrell, 1996. Alternative Adhesion Sites in Human Fibrinogen for Vascular Endothelial Cells. Biochemistry 35(13), 4169-4175.

Rooney, P., Kumar, S., Ponting, J., Wang, M., 1995. The role of hyaluronan in tumour neovascularization. Int. J. Cancer 60, 632-636.

Sattar, A., Rooney, P., Kumar, S., Pye, D., West, D. c., Scott, I., Ledger, P., 1994. Application of angiogenic oligosaccharides of hyaluronan increase blood vessel numbers in rat skin. J. Invest. Dermatol. 103, 576-579.

Shay Soker, Marcos Machado, Anthony Atala, 2000. Systems for therapeutic angiogenesis in tissue engineering. World J Urol 18, 10-18.

Sieminski A. L., Hebbel R. P., Gooch K. J., 2004. The relative magnitudes of endothelial force generation and matrix stiffness modulate capillary morphogenesis in vitro. Experimental cell research 297, 574-584.

Tammi, M. I., Day, A. J., Turkley, E. A., 2002. Hyaluronan and homeostasis: a balancing act. J. Biol. Chem. 277, 4581-4584.

Tamer A. E. Ahmed, May Griffith, Max Hincke, 2007. Characterization and inhibition of fibrin hydrogel-degrading enzymes during development of tissue engineering scaffolds. Tissue Engineering 13(7), 1469-1477.

Vinata B. L., Marie G. S., 2000. Differences in hyaluronic acid-mediated functions and signaling in arterial, microvessel, and vein-derived human endothelial cells. Journal of biological chemistry 275, 27641-27649.

Volker Nehls and Detlev Drenckhahn, 1995. A novel, microcarrier-based in vitro assay for rapid and reliable quantification of three-dimensional cell migration and angiogenesis. Microvascular research 50, 311-322.

Volker Nehls and Rita Herrmann, 1995. The configuration of fibrin clots determines capillary morphogenesis and endothelial cell migration. Microvascular research 51, 347-364.

Wiebke Hayen, Matthias Goebeler, Shant Kumar, Reimer Rieben, Volker Nehls, 1999. Hyaluronan stimulates tumor cell migration by modulating the fibrin fiber architecture. Journal of cell science 112, 2241-2251.

Ye Q., Zund G. I, Benedikt P., Jockenhoevel S., Hoerstrup S. P., Sakyama S., Hubbell J. A., Turina M., 2000. Fibrin gel as a three dimensional matrix in cardiovascular tissue engineering. European Journal of Cardio-Thoracic Surgery 17(5), 587-591.

Zhao, H., et al., A polylactide/fibrin gel composite scaffold for cartilage tissue engineering: fabrication and an in vitro evaluation. J Mater Sci Mater Med, 2009. 20(1): 135-43.

What is claimed is:

1. An angiogenesis support hydrogel comprising a cross-linked network of a hyaluronic-tyramine conjugate interpenetrated by fibrin fibers, the hyaluronic-tyramine conjugate cross-linked by oxidative coupling between tyramine groups, the hydrogel formed from a mixture comprising the hyaluronic-tyramine conjugate at a concentration of 1 mg/ml to 10 mg/ml, a peroxidase at a concentration of 0.05 unit/ml to 0.5 unit/ml, hydrogen peroxide at a concentration of 20 µM to 500 µM, fibrinogen at a concentration of 1 mg/ml to 10 mg/ml, and thrombin at a concentration of 0.1 unit/ml to 1.0 unit/ml.

2. The hydrogel of claim 1, wherein the mixture from which the hydrogel is formed further comprises endothelial cells.

3. The hydrogel of claim 2, wherein the endothelial cells are capable of undergoing angiogenesis.

4. The hydrogel of claim 1, wherein the mixture from which the hydrogel is formed further comprises an angiogenic protein.

5. The hydrogel of claim 1, wherein the mixture from which the hydrogel is formed further comprises a therapeutic agent.

6. A method of promoting angiogenesis, the method comprising:
contacting a population of cells capable of undergoing angiogenesis with the hydrogel of claim 1 under conditions sufficient for the population of cells to undergo angiogenesis.

7. The method of claim 6, wherein the population of cells is encapsulated in the hydrogel.

8. The method of claim 6, wherein the population of cells is in vitro.

9. The method of claim 6, wherein the population of cells is in a subject, said contacting comprising administering the hydrogel to the subject.

10. The method of claim 7, further comprising administering the hydrogel to a subject.

11. A method of culturing a cell, the method comprising contacting a cell with the hydrogel of claim 1 under conditions sufficient for the population of cells to grow.

* * * * *